(12) United States Patent
Sato et al.

(10) Patent No.: US 8,827,897 B2
(45) Date of Patent: Sep. 9, 2014

(54) ENDOSCOPE

(75) Inventors: Yoshinori Sato, Hachioji (JP); Eiji Matsuda, Sagamihara (JP); Toru Shinmura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 240 days.

(21) Appl. No.: 13/073,267

(22) Filed: Mar. 28, 2011

(65) Prior Publication Data

US 2011/0237891 A1    Sep. 29, 2011

Related U.S. Application Data

(63) Continuation of application No. PCT/JP2010/067886, filed on Oct. 12, 2010.

(30) Foreign Application Priority Data

Oct. 30, 2009   (JP) ................................ 2009-251337

(51) Int. Cl.
*A61B 1/00* (2006.01)

(52) U.S. Cl.
USPC ........... 600/146; 600/139; 600/141; 600/149; 600/150

(58) Field of Classification Search
USPC ................................. 600/146, 149
See application file for complete search history.

(56) References Cited

U.S. PATENT DOCUMENTS

| | | | | |
|---|---|---|---|---|
| 3,788,303 A | * | 1/1974 | Hall | 600/148 |
| 3,897,775 A | * | 8/1975 | Furihata | 600/131 |
| 4,688,555 A | * | 8/1987 | Wardle | 600/149 |
| 4,718,407 A | * | 1/1988 | Chikama | 600/150 |
| 4,905,666 A | * | 3/1990 | Fukuda | 600/146 |
| 5,167,221 A | * | 12/1992 | Chikama | 600/149 |
| 5,179,935 A | * | 1/1993 | Miyagi | 600/142 |
| 5,388,568 A | * | 2/1995 | van der Heide | 600/146 |

(Continued)

FOREIGN PATENT DOCUMENTS

| | | |
|---|---|---|
| CN | 101475045 A | 7/2009 |
| JP | U 1-133902 | 9/1989 |

(Continued)

OTHER PUBLICATIONS

International Search Report issued in PCT/JP2010-067886, mailed Dec. 14, 2010. (with English-language translation).

(Continued)

*Primary Examiner* — Matthew J Kasztejna
(74) *Attorney, Agent, or Firm* — Oliff PLC (57) ABSTRACT

An endoscope includes a curving operation portion which performs a curving operation of a curving portion by rotating around a pivot shaft in a first rotation direction and in a second rotation direction opposite to the first rotation direction from a neutral position where the curving portion is in a non-curved neutral state, a first operation wire which is pulled by the curving operation in the curving operation portion to curve the curving portion in the second curving direction, and a second operation wire which is pulled by the curving operation in the curving operation portion to curve the curving portion in the first curving direction. The endoscope includes a wire crossing portion in which the second operation wire crosses the first operation wire, and a movement regulating portion which regulates the movement of the wire crossing portion from within the operation portion into the insertion portion.

2 Claims, 8 Drawing Sheets

(56) References Cited

U.S. PATENT DOCUMENTS

| | | | |
|---|---|---|---|
| 5,960,145 A * | 9/1999 | Sanchez | 385/116 |
| 6,942,613 B2 * | 9/2005 | Ewers et al. | 600/114 |
| 7,842,028 B2 * | 11/2010 | Lee | 606/1 |
| 2010/0160736 A1 * | 6/2010 | Padget et al. | 600/142 |

FOREIGN PATENT DOCUMENTS

| | | |
|---|---|---|
| JP | A 2-114929 | 4/1990 |
| JP | A 3-060625 | 3/1991 |
| JP | U 4-801 | 1/1992 |
| JP | A 2000-126119 | 5/2000 |
| JP | A 2005-065931 | 3/2005 |
| JP | A 2007-282693 | 11/2007 |

OTHER PUBLICATIONS

Aug. 23, 2013 Office Action issued in Chinese Patent Application No. 201080005611.5 (w/English Translation).

\* cited by examiner

ENDOSCOPE

CROSS REFERENCE TO RELATED APPLICATIONS

This is a Continuation Application of PCT Application No. PCT/JP2010/067886, filed Oct. 12, 2010, which was published under PCT Article 21(2) in Japanese.

This application is based upon and claims the benefit of priority from prior Japanese Patent Application No. 2009-251337, filed Oct. 30, 2009, the entire contents of which are incorporated herein by reference.

BACKGROUND OF THE INVENTION

1. Field of the Invention

The present invention relates to an endoscope in which an operation wire is pulled by a curving operation in a curving operation portion provided in an operation portion to curve a curving portion.

2. Description of the Related Art

In general, a medical endoscope includes a curving portion provided in a part of the distal direction side of an insertion portion to be inserted into a body cavity. In an operation portion which is provided in a proximal direction side to the insertion portion, a curving operation portion such as a curving operation knob or a curving operation lever which performs a curving operation of the curving portion is provided rotatably around a pivot shaft. An operation wire for the curving operation is provided within the insertion portion and within the operation portion. The operation wire is pulled by the curving operation in the curving operation portion to curve the curving portion.

For example, Jpn. Pat. Appln. KOKAI Publication No. 2000-126119 shows an endoscope including a two-way curving mechanism in which a curving portion is curved in a first curving direction and in a second curving direction opposite to the first curving direction. In this endoscope, the curving portion is curved in the first curving direction or the second curving direction by rotating a curving operation lever as a curving operation portion. The curving operation lever is capable of rotating in a first rotation direction and in a second rotation direction opposite to the first rotation direction. The relationship between the rotation direction of the curving operation lever and the curving direction of the curving portion is set, for example, as follows: The curving portion is curved in the first curving direction by rotating the curving operation lever in the first rotation direction. The curving portion is curved in the second curving direction by rotating the curving operation lever in the second rotation direction. The condition in which the curving operation is performed as mentioned above is referred to as a first set condition.

On the other hand, the relationship between the rotation direction of the curving operation lever and the curving direction of the curving portion varies depending on user preference. It is therefore desired to provide an endoscope in which the relationship between the rotation direction of the curving operation lever and the curving direction of the curving portion is adaptable to the user preference. For example, the following types of endoscopes including the two-way curving mechanisms are used; a type that performs the curving operation in the first set condition; and a type that performs the curving operation in a second set condition in which the relationship between the rotation direction of the curving operation lever and the curving direction of the curving portion is opposite to that of the first set condition. In the second set condition, the curving portion is curved in the second curving direction by rotating the curving operation lever in the first rotation direction. The curving portion is curved in the first curving direction by rotating the curving operation lever in the second rotation direction. A user selectively uses one of the types in the first set condition and the second set condition suitably to his/her preference.

Moreover, an endoscope provided with a wire crossing portion in which two operation wires cross each other in an operation portion is disclosed in Jpn. Pat. Appln. KOKAI Publication No. 2005-65931. The wire crossing portion is provided so that the relationship between the rotation direction of the curving operation lever and the curving direction of the curving portion is opposite to that in the case where no wire crossing portion is provided.

BRIEF SUMMARY OF THE INVENTION

According to one aspect of the invention, an endoscope includes: an insertion portion which includes a curving portion configured to curve in a first curving direction and in a second curving direction opposite to the first curving direction; an operation portion provided in a proximal direction side to the insertion portion, the operation portion including a curving operation portion which is configured to perform a curving operation of the curving portion by rotating around a pivot shaft in a first rotation direction and in a second rotation direction opposite to the first rotation direction from a neutral position where the curving portion is in a non-curved neutral state; a first operation wire which is pulled by the curving operation in the curving operation portion to curve the curving portion in the second curving direction; a second operation wire which is pulled by the curving operation in the curving operation portion to curve the curving portion in the first curving direction; a wire crossing portion which is provided within the operation portion and in which the second operation wire crosses the first operation wire; and a movement regulating portion which is provided within the operation portion and which is configured to regulate the movement of the wire crossing portion from within the operation portion into the insertion portion.

According to one other aspect of the invention, an endoscope includes: an insertion portion which includes a curving portion configured to curve in a first curving direction and in a second curving direction opposite to the first curving direction; an operation portion provided in a proximal direction side to the insertion portion, the operation portion including curving operation means for performing a curving operation of the curving portion by rotating around a pivot shaft in a first rotation direction and in a second rotation direction opposite to the first rotation direction from a neutral position where the curving portion is in a non-curved neutral state; a first operation wire which is pulled by the curving operation in the curving operation means to curve the curving portion in the second curving direction; a second operation wire which is pulled by the curving operation in the curving operation means to curve the curving portion in the first curving direction; a wire crossing portion which is provided within the operation portion and in which the second operation wire crosses the first operation wire; and movement regulating means for regulating the movement of the wire crossing portion from within the operation portion into the insertion portion, the movement regulating means being provided within the operation portion.

Advantages of the invention will be set forth in the description which follows, and in part will be obvious from the description, or may be learned by practice of the invention.

Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
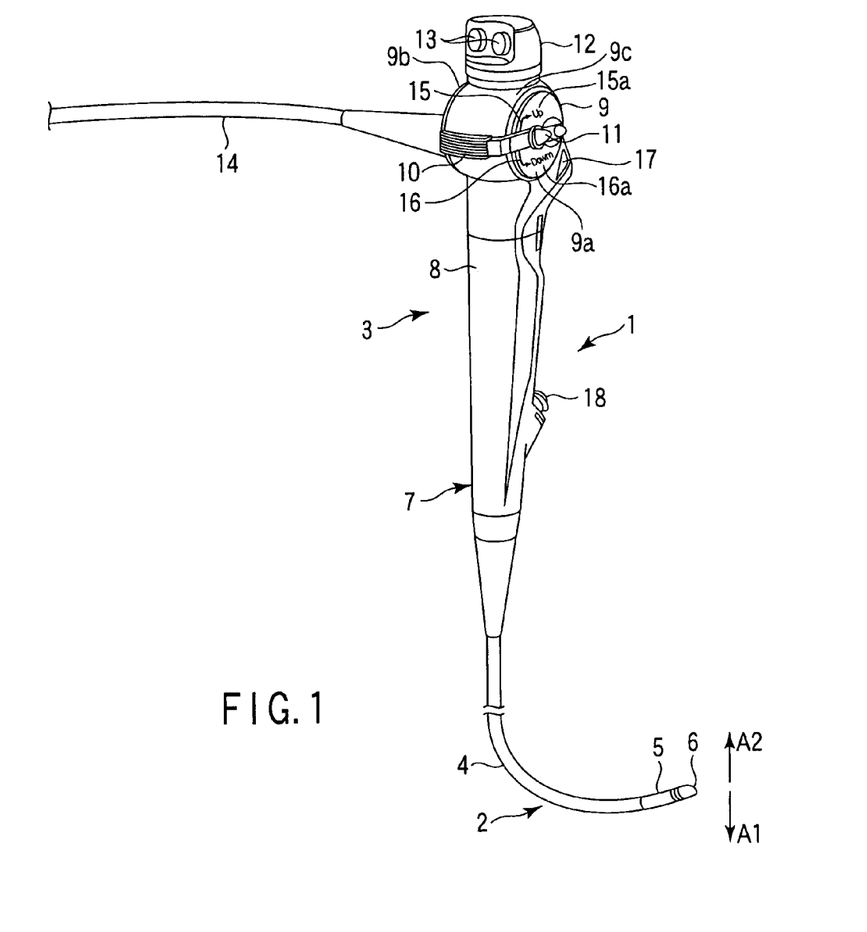
FIG. 1 is a perspective view showing a schematic configuration of an endoscope according to a first embodiment of the present invention.

A first embodiment of the present invention will be described hereinafter with reference to FIG. 1 to FIG. 5B. FIG. 1 is a diagram showing a schematic configuration of an endoscope 1 according to the first embodiment. As shown in FIG. 1, the endoscope 1 includes an elongated insertion portion 2 to be inserted into a body cavity, and an operation portion 3 coupled to the proximal direction side of the insertion portion 2. The insertion portion 2 includes a flexible tubular portion 4, a curving portion 5, and a distal hard portion 6 in order from the proximal direction side. The curving portion 5 is formed by, for example, a two-way curving type curving tube, and is capable of curving in a first curving direction (direction of arrow A1 in FIG. 1) and in a second curving direction (direction of arrow A2 in FIG. 1) opposite to the first curving direction. The distal hard portion 6 is provided with, for example, an observation window, an illumination window, and an opening of a medical treatment instrument insertion channel (none of which is shown).

The flexible tubular portion 4 of the insertion portion 2 includes a spiral tube (flex) formed by spirally winding a metal belt-like material, a woven tube (braid) which is provided on the outer peripheral side of the spiral tube and which is formed by weaving, for example, a metal wire, and an envelope which is stacked on the outer peripheral side of the woven tube and which is made of, for example, a thermoplastic elastomer.

The operation portion 3 includes an operation portion main body 7. A grip portion 8 is formed by the outer peripheral surface of the operation portion main body 7. A substantially columnar lever attachment portion 9 is provided to the side of the grip portion 8 opposite to the insertion portion 2 to continue to the grip portion 8. The lever attachment portion 9 includes two planes 9a and 9b and a curved surface 9c. A curving operation lever 10 is provided in the plane 9a of the lever attachment portion 9, and is a curving operation portion which performs a curving operation to curve the curving portion 5 in the first curving direction or the second curving direction. The curving operation lever 10 is exposed, and provided rotatably around a pivot shaft 11. A protruding portion 12 is provided in the curved surface 9c of the lever attachment portion 9. For example, a photographic operation button 13 is provided in the protruding portion 12.

Figure 2:
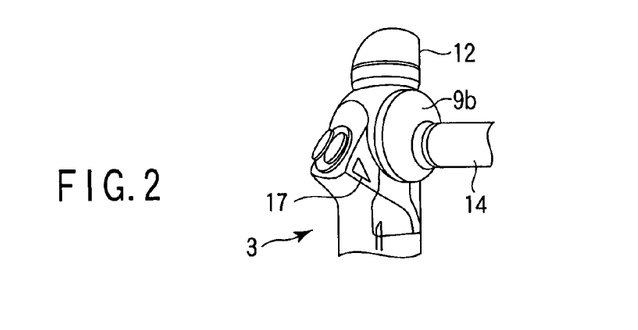
FIG. 2 is a perspective view showing the appearance of an operation portion of the endoscope according to the first embodiment.

As shown in FIG. 2, one end of a universal cord 14 is coupled to the plane 9b of the lever attachment portion 9. A connector portion (not shown) to be coupled to a light source device (not shown) or an image processor (not shown) is provided on the other end of the universal cord 14. Moreover, the grip portion 8 is provided with a medical treatment instrument insertion portion 18. A medical treatment instrument insertion opening 18a (see FIG. 5B) of the medical treatment instrument insertion portion 18 is in communication with the medical treatment instrument insertion channel (not shown) provided within the insertion portion 2.

The curving operation lever 10 of the present embodiment is described below. Suppose that the endoscope 1 is used so that the operation portion 3 is disposed to the upper side of the insertion portion 2 as shown in FIG. 1. In this case, when the curving portion 5 is in a non-curved neutral state, the curving operation lever 10 is held at a neutral position to extend substantially horizontally from the pivot shaft 11. When the curving operation lever 10 is rotated upward (in a first rotation direction) from the neutral position, the curving portion 5 is curved in the first curving direction (direction of arrow A1 in FIG. 1) from the neutral state. When the curving operation lever 10 is rotated downward (in a second rotation direction) from the neutral position, the curving portion 5 is curved in the second curving direction (direction of arrow A2 in FIG. 1) from the neutral state. The condition in which the curving operation of the curving portion 5 is performed as mentioned above is referred to as a first set condition of a curving mechanism 30 (described later). Here, the first curving direction is a downward direction when, for example, the curving portion 5 extends substantially horizontally, and the second curving direction is an upward direction when, for example, the curving portion 5 extends substantially horizontally.

An upward arrow indication portion 15 and a downward arrow indication portion 16 are provided in the plane 9a of the lever attachment portion 9 along the rotation track of the curving operation lever 10. A legend indication portion 15a indicating, for example, the legend "UP" is provided in the upward arrow indication portion 15. A legend indication portion 16a indicating, for example, the legend "DOWN" is provided in the downward arrow indication portion 16. Moreover, the operation portion main body 7 of the operation portion 3 is provided with substantially triangular set condition indication portions 17 which indicate that the curving mechanism 30 (described later) is in a second set condition (described later). The set condition indication portions 17 are respectively provided on both sides of a part of the operation portion main body 7 located in the vicinity of the lever attachment portion 9.

Here, the set condition of the curving mechanism 30 during the curving operation to curve the curving portion 5 in response to the rotation of the curving operation lever 10 is described. The relationship between the rotation direction of the curving operation lever 10 and the curving direction of the curving portion 5 is set as follows. As described above, in the first set condition of the curving mechanism 30, the curving portion 5 is curved in the first curving direction (direction of arrow A1 in FIG. 1) from the neutral state when the curving operation lever 10 is rotated upward (in the first rotation direction) from the neutral position. The curving portion 5 is curved in the second curving direction (direction of arrow A2 in FIG. 1) from the neutral state when the curving operation lever 10 is rotated downward (in the second rotation direction) from the neutral position. Meanwhile, in the second set condition, the curving portion 5 is curved in the second curving direction (direction of arrow A2 in FIG. 1) from the neutral state when the curving operation lever 10 is rotated upward (in the first rotation direction) from the neutral position. The curving portion 5 is curved in the first curving direction (direction of arrow A1 in FIG. 1) from the neutral state when the curving operation lever 10 is rotated downward (in the second rotation direction) from the neutral position.

Figure 3A:
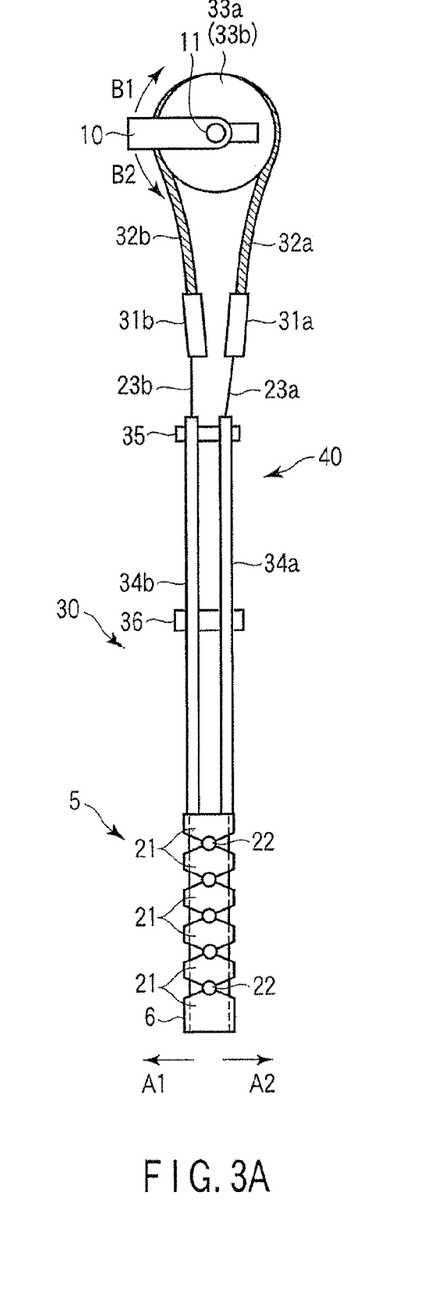
FIG. 3A is a schematic diagram showing the configuration of a curving mechanism of the endoscope according to the first embodiment in a first set condition.

FIG. 3A is a diagram schematically showing the curving mechanism 30. In the curving portion 5, curving pieces 21 are provided side by side in the longitudinal direction of the insertion portion 2. Adjacent curving pieces 21 are connected via a pin 22 pivotally with respect to each other. The curving piece 21 located to a most distal direction side is connected to the proximal end of the main body member of the distal hard portion 6. A woven tube (not shown) in which, for example, a metal wire is woven is provided on the outer peripheral side of each of the curving pieces 21. An envelope (not shown) made of an elastic resin is stacked on the outer peripheral side of the woven tube, and forms the exterior of the curving portion 5.

The distal ends of a first operation wire 23a and a second operation wire 23b for the curving operation are fixed by, for example, solder to the curving piece 21 located to the most distal direction side. A first wire guide ring (not shown) through which the first operation wire 23a is inserted and a second wire guide ring (not shown) through which the second operation wire 23b is inserted are formed in the peripheral wall portion of each of the curving pieces 21. The first operation wire 23a is guided to the flexible tubular portion 4 through the first wire guide ring of each of the curving pieces 21. Likewise, the second operation wire 23b is guided to the flexible tubular portion 4 through the second wire guide ring of each of the curving pieces 21. Each of the first and second wire guide rings is formed into a ring shape, for example, by deforming a part of the peripheral wall of the curving piece 21 toward an inner peripheral side with respect to other parts.

The first operation wire 23a and the second operation wire 23b are guided into the operation portion 3 through the curving portion 5 and the flexible tubular portion 4. The proximal end of the first operation wire 23a is connected to one of a first connection member 31a and a second connection member 31b in accordance with the set condition of the curving mechanism 30. The proximal end of the second operation wire 23b is connected to one of the first connection member 31a and the second connection member 31b to which the first operation wire 23a is not connected, in accordance with the set condition of the curving mechanism 30. A first draw-wire 32a is connected to the proximal direction side of the first connection member 31a, and a second draw-wire 32b is connected to the proximal direction side of the second connection member 31b. The first draw-wire 32a is passed around a first pulley 33a as a wire drive portion, and the second draw-wire 32b is passed around a second pulley 33b as a wire drive portion. In addition, a slack adjustment mechanism (not shown) which adjusts the slack of the first operation wire 23a is incorporated in the first connection member 31a, and a slack adjustment mechanism (not shown) which adjusts the slack of the second operation wire 23b is incorporated in the second connection member 31b.

Figure 4:
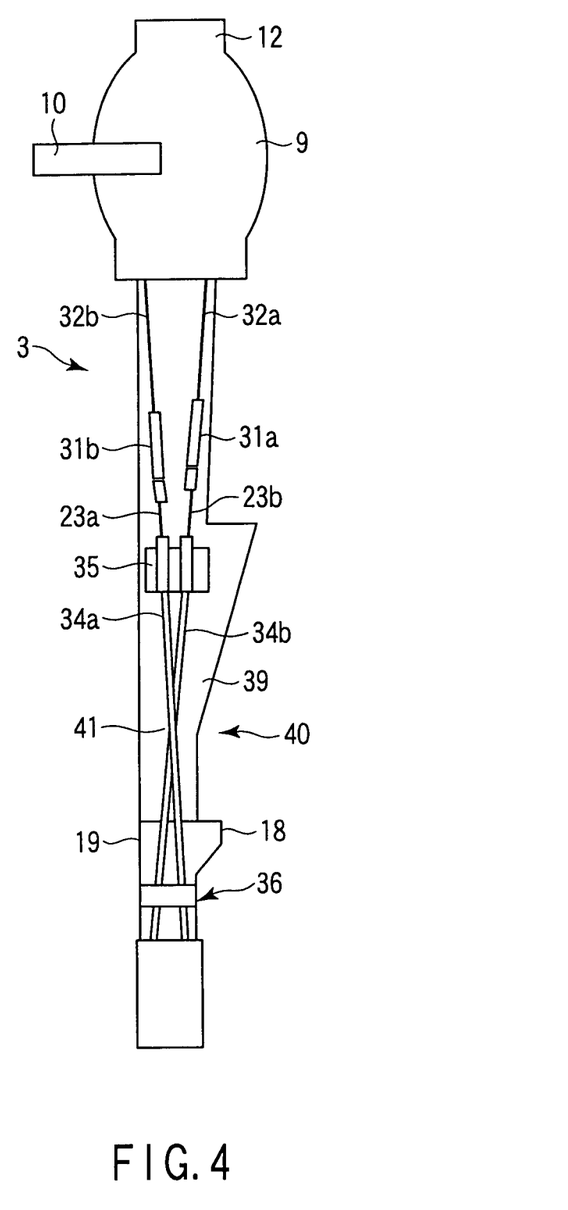
FIG. 4 is a schematic diagram showing the configuration of operation wires provided within the operation portion of the endoscope according to the first embodiment in the second set condition.

A first wire guide 34a through which the first operation wire 23a is inserted and a second wire guide 34b through which the second operation wire 23b is inserted are provided within the flexible tubular portion 4. The first wire guide 34a and the second wire guide 34b are formed by tightly wound coils. The distal ends of the first wire guide 34a and the second wire guide 34b are firmly fixed by, for example, solder to the curving piece 21 located to the most proximal direction side. The proximal ends of the first wire guide 34a and the second wire guide 34b are fixed to a wire guide fixing member (wire guide fixing portion) 35 provided within the operation portion 3. As shown in FIG. 4, the wire guide fixing member 35 is fixed to a flat base plate 39 which is a frame fixed within the operation portion 3.

The curving mechanism 30 includes the first pulley 33a around which the first draw-wire 32a is passed, and the second pulley 33b around which the second draw-wire 32b is passed. The first draw-wire 32a is passed around the first pulley 33a from a second curving direction side (right side in FIG. 3A and FIG. 3B), and the proximal end (terminal end) thereof is firmly fixed by, for example, solder to the peripheral wall of the first pulley 33a. The second draw-wire 32b is passed around the second pulley 33b from a first curving direction side (left side in FIG. 3A and FIG. 3B), and the proximal end (terminal end) thereof is firmly fixed by, for example, solder to the peripheral wall of the second pulley 33b.

The pivot shaft 11 of the curving operation lever 10 is fixed to the central positions of the first pulley 33a and the second pulley 33b. By rotating the curving operation lever 10, the first pulley 33a and the second pulley 33b pivot together with the pivot shaft 11 of the curving operation lever 10. As a result, one of the first draw-wire 32a fixed to the first pulley 33a and the second draw-wire 32b fixed to the second pulley 33b is pulled. When the first draw-wire 32a is pulled, one of the first operation wire 23a and the second operation wire 23b that is connected to the first draw-wire 32a is pulled. Likewise, when the second draw-wire 32b is pulled, one of the first operation wire 23a and the second operation wire 23b that is connected to the second draw-wire 32b is pulled. The first operation wire 23a or the second operation wire 23b is pulled such that the curving piece 21 located to the most distal direction side to which the first operation wire 23a and the second operation wire 23b are coupled, and the distal hard portion 6 to which the curving piece 21 located to the most distal direction side is connected are pulled. Thus, each of the curving pieces 21 pivots on the pin 22, and the curving portion 5 is curved in the first curving direction or the second curving direction. Here, when the first operation wire 23a is pulled, the curving portion 5 is curved in the second curving direction (direction of arrow A2 in FIG. 3A and FIG. 3B). When the second operation wire 23b is pulled, the curving portion 5 is curved in the first curving direction (direction of arrow A1 in FIG. 3A and FIG. 3B).

FIG. 3A is a diagram showing the curving mechanism 30 of the endoscope 1 in the first set condition. In the first set condition, the first operation wire 23a is connected to the first draw-wire 32a, and the second operation wire 23b is connected to the second draw-wire 32b. As described above, in the first set condition, the curving portion 5 is curved in the first curving direction (direction of arrow A1 in FIG. 3A) from the neutral state when the curving operation lever 10 is rotated in a direction of arrow B1 in FIG. 3A (in the first rotation direction) from the neutral position. On the other hand, the curving portion 5 is curved in the second curving direction (direction of arrow A2 in FIG. 3A) from the neutral state when the curving operation lever 10 is rotated in a direction of arrow B2 in FIG. 3A (in the second rotation direction) from the neutral position.

That is, when the curving operation lever 10 is rotated in the direction of arrow B1 in FIG. 3A (in the first rotation direction), the second draw-wire 32b is pulled. Thus, the second operation wire 23b connected to the second draw-wire 32b is pulled. As the second operation wire 23b is pulled, the curving portion 5 is curved in the first curving direction (direction of arrow A1 in FIG. 3A).

On the other hand, when the curving operation lever 10 is rotated in the direction of arrow B2 in FIG. 3A (in the second rotation direction), the first draw-wire 32a is pulled. Thus, the first operation wire 23a connected to the first draw-wire 32a is pulled. As the first operation wire 23a is pulled, the curving portion 5 is curved in the second curving direction (direction of arrow A2 in FIG. 3A).

Figure 3B:
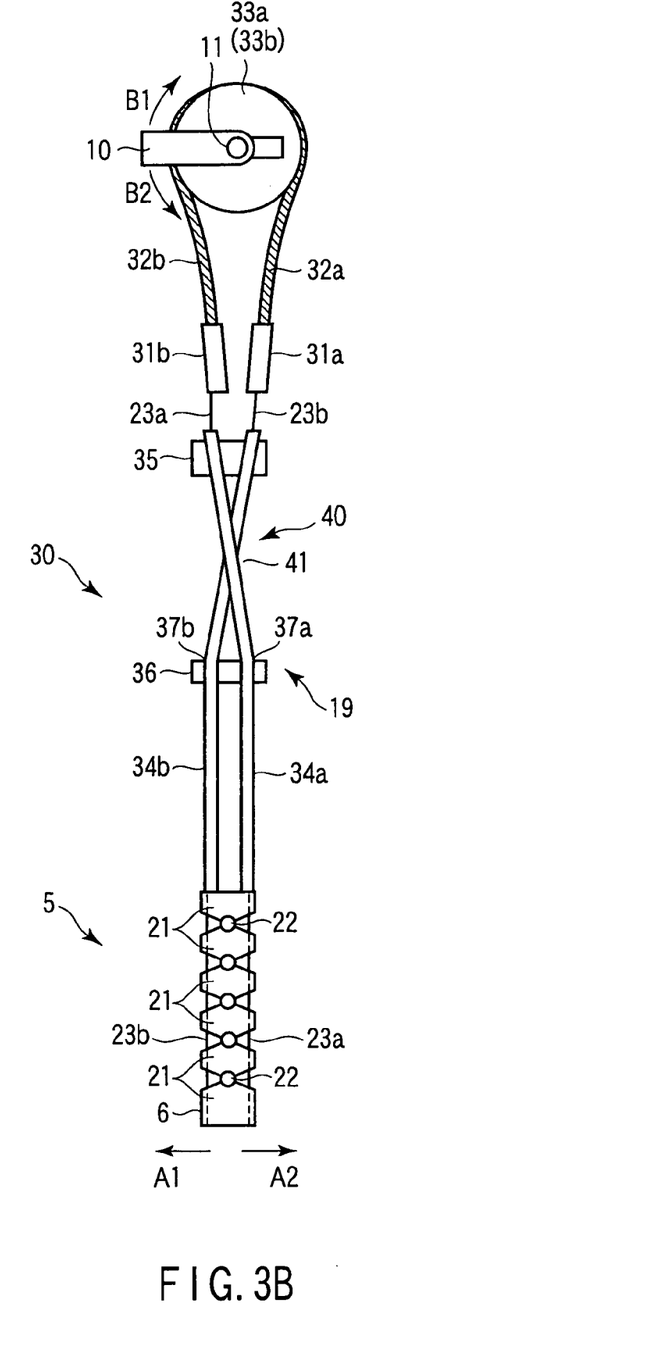
FIG. 3B is a schematic diagram showing the configuration of the curving mechanism of the endoscope according to the first embodiment in a second set condition.

FIG. 3B is a diagram showing the curving mechanism 30 of the endoscope 1 of the present embodiment in the second set condition. In the second set condition, the first operation wire 23a is connected to the second draw-wire 32b, and the second operation wire 23b is connected to the first draw-wire 32a. As described above, in the second set condition, the curving portion 5 is curved in the second curving direction (direction of arrow A2 in FIG. 3B) from the neutral state when the curving operation lever 10 is rotated in a direction of arrow B1 in FIG. 3B (in the first rotation direction) from the neutral position. On the other hand, the curving portion 5 is curved in the first curving direction (direction of arrow A1 in FIG. 3B) from the neutral state when the curving operation lever 10 is rotated in a direction of arrow B2 in FIG. 3B (in the second rotation direction) from the neutral position.

That is, when the curving operation lever 10 is rotated in the direction of arrow B1 in FIG. 3B (in the first rotation direction), the second draw-wire 32b is pulled. Thus, the first operation wire 23a connected to the second draw-wire 32b is pulled. As the first operation wire 23a is pulled, the curving portion 5 is curved in the second curving direction (direction of arrow A2 in FIG. 3B).

On the other hand, when the curving operation lever 10 is rotated in the direction of arrow B2 in FIG. 3B (in the second rotation direction), the first draw-wire 32a is pulled. Thus, the second operation wire 23b connected to the first draw-wire 32a is pulled. As the second operation wire 23b is pulled, the curving portion 5 is curved in the first curving direction (direction of arrow A1 in FIG. 3A).

As described above, the curving mechanism 30 of the endoscope of the present embodiment includes a curving direction setting portion 40 which sets the relationship between the rotation direction of the curving operation lever 10 and the curving direction of the curving portion 5 to the first set condition or the second set condition. The curving direction setting portion 40 includes a wire crossing portion 41 which is provided within the operation portion 3 and which crosses the first wire guide 34a (first operation wire 23a) and the second wire guide 34b (second operation wire 23b) in the second set condition. The curving mechanism 30 includes a movement regulating portion 36 which is provided within the operation portion 3 and which regulates the movement of the wire crossing portion 41 from within the operation portion 3 into the insertion portion 2.

Figure 5A:
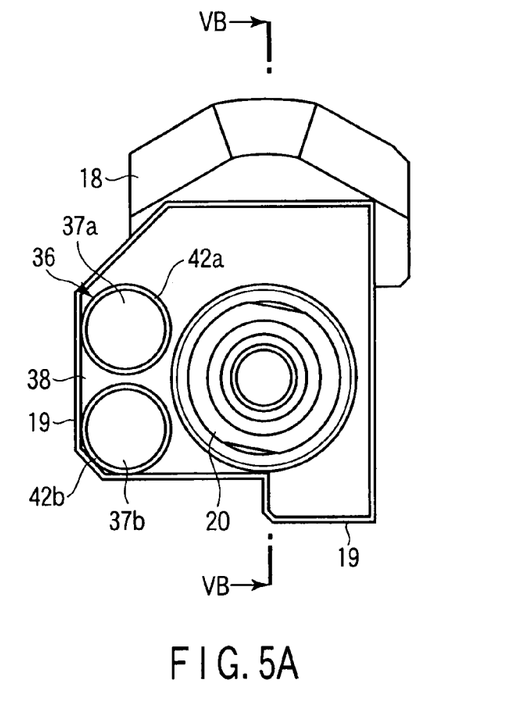
FIG. 5A is a front view showing a coupling member provided in a connection portion between a medical treatment instrument insertion channel and a medical treatment instrument insertion portion of the endoscope according to the first embodiment.
Figure 5B:
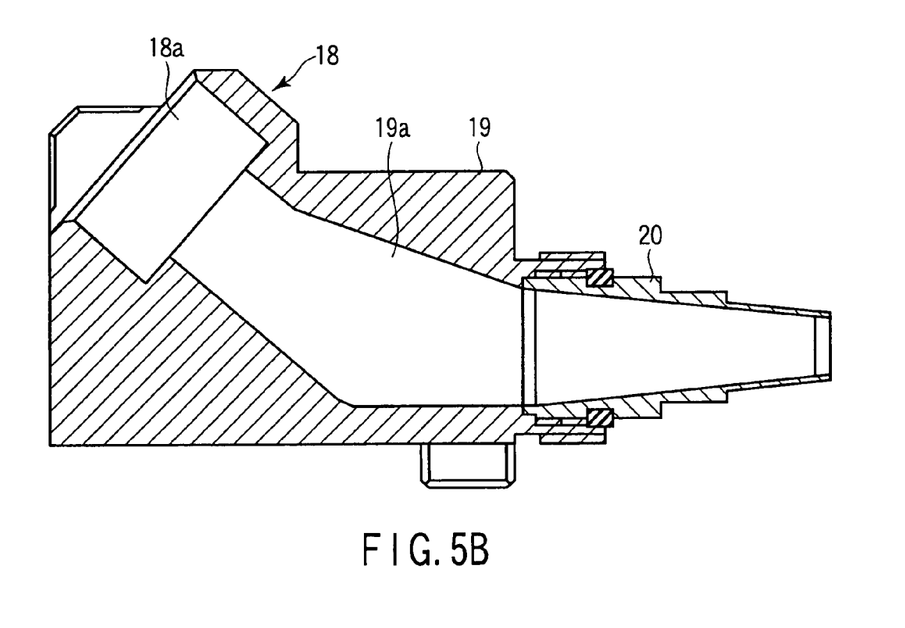
FIG. 5B is a sectional view along the line VB-VB in FIG. 5A.

As shown in FIG. 5B, a coupling member 19 as a block is provided in the medical treatment instrument insertion portion 18 of the operation portion 3. A medical treatment instrument insertion path 19a is formed in the coupling member 19. As shown in FIG. 5A, a connection cap 20 is coupled to the coupling member 19 via a screw portion (not shown). The connection cap 20 is coupled to the coupling member 19 in a state that the connection cap 20 is inserted in the medical treatment instrument insertion path 19a. The coupling member 19 is provided with a first inner peripheral surface portion 42a that defines a first hole portion 37a, and a second inner peripheral surface portion 42b that defines a second hole portion 37b. The medical treatment instrument insertion path 19a is provided at a distance from the first inner peripheral surface portion 42a and the second inner peripheral surface portion 42b. The inside of the connection cap 20 is in communication with the medical treatment instrument insertion channel (not shown) within the insertion portion 2.

The first wire guide 34a is inserted through the first hole portion 37a of the coupling member 19, and the second wire guide 34b is inserted through the second hole portion 37b. A partition wall 38 is provided between the first hole portion 37a and the second hole portion 37b of the coupling member 19. The movement regulating portion 36 which regulates the movement of the wire crossing portion 41 is formed by the partition wall 38.

Now, the function of the above configuration is described. The curving direction setting portion 40 of the present embodiment sets the relationship between the rotation direction of the curving operation lever 10 and the curving direction of the curving portion 5 to the first set condition or the second set condition during the curving operation performed with the curving operation lever 10. When the curving operation lever 10 is rotated in the direction of arrow B1 in FIG. 3A and FIG. 3B (in the first rotation direction), the second draw-wire 32b is pulled. In the first set condition, the second operation wire 23b is connected to the second draw-wire 32b via the second connection member 31b. Thus, as the second draw-wire 32b is pulled, the second operation wire 23b is pulled, and the curving portion 5 is curved in the first curving direction (direction of arrow A1 in FIG. 3A). On the other hand, in the second set condition, the first operation wire 23a is connected to the second draw-wire 32b via the second connection member 31b. Thus, as the second draw-wire 32b is pulled, the first operation wire 23a is pulled, and the curving portion 5 is curved in the second curving direction (direction of arrow A2 in FIG. 3B).

When the curving operation lever 10 is rotated in the direction of arrow B2 in FIG. 3A and FIG. 3B (in the second rotation direction), the first draw-wire 32a is pulled. In the first set condition, the first operation wire 23a is connected to the first draw-wire 32a via the first connection member 31a. Thus, as the first draw-wire 32a is pulled, the first operation wire 23a is pulled, and the curving portion 5 is curved in the second curving direction (direction of arrow A2 in FIG. 3A). On the other hand, in the second set condition, the second operation wire 23b is connected to the first draw-wire 32a via the first connection member 31a. Thus, as the first draw-wire 32a is pulled, the second operation wire 23b is pulled, and the curving portion 5 is curved in the first curving direction (direction of arrow A1 in FIG. 3B).

Thus, the configuration described above has the following advantages. That is, according to the present embodiment, during the curving operation performed with the curving operation lever 10, the curving direction setting portion 40 within the operation portion 3 sets the relationship between the rotation direction of the curving operation lever 10 and the curving direction of the curving portion 5. The curving direction setting portion 40 includes the wire crossing portion 41 which crosses the first operation wire 23a and the second operation wire 23b that are extended from the insertion portion 2 into the operation portion 3 in the second set condition. The wire crossing portion 41 is provided so that in the second set condition, the relationship between the rotation direction of the curving operation lever 10 and the curving direction of the curving portion 5 is opposite to that in the first set condition as described above. As a result, two types different in the relationship between the rotation direction of the curving operation lever 10 and the curving direction of the curving portion 5 can be easily prepared without using components that are not shared. That is, when two types different in the relationship between the rotation direction of the curving operation lever 10 and the curving direction of the curving portion 5 are produced, the relationship between the rotation direction of the curving operation lever 10 and the curving direction of the curving portion 5 can be reversed using the same components for the two types. Consequently, common components can be used for the two types, and costs can be reduced.

Furthermore, the first operation wire 23a is inserted through the first wire guide 34a, and the second operation wire 23b is inserted through the second wire guide 34b. In the wire crossing portion 41, the first wire guide 34a and the second wire guide 34b cross each other. Therefore, the first operation wire 23a and the second operation wire 23b do not directly contact each other in the wire crossing portion 41. As a result, wearing of the first operation wire 23a and the second operation wire 23b can be inhibited. Moreover, the movement regulating portion 36 regulates the movement of the wire crossing portion 41 from within the operation portion 3 into the insertion portion 2. Thus, even when the curving operation is repeated, the movement of the wire crossing portion 41 from within the operation portion 3 into the insertion portion 2 can be prevented. This makes it possible to prevent the interference between the wire crossing portion 41 and components provided within the insertion portion 2 including an imaging cable, the medical treatment instrument insertion channel, a light guide, and an air/water supply tube. Thus, damage to the components provided within the insertion portion 2 including the imaging cable, the medical treatment instrument insertion channel, the light guide, and the air/water supply tube can be prevented.

The movement regulating portion 36 is formed by the partition wall 38 between the first inner peripheral surface portion 42a and the second inner peripheral surface portion 42b of the coupling member 19. Therefore, the number of components can be smaller and the configuration can be simpler than when the movement regulating portion 36 is formed in a single component independent of, for example, the coupling member 19. Moreover, the first hole portion 37a defined by the first inner peripheral surface portion 42a and the second hole portion 37b defined by the second inner peripheral surface portion 42b can be drilled in the coupling member 19 by a drill press. Thus, processing costs can be lower than when a long hole through which the first wire guide 34a and the second wire guide 34b are inserted together is formed by end mill machining.

Second Embodiment

Figure 6A:
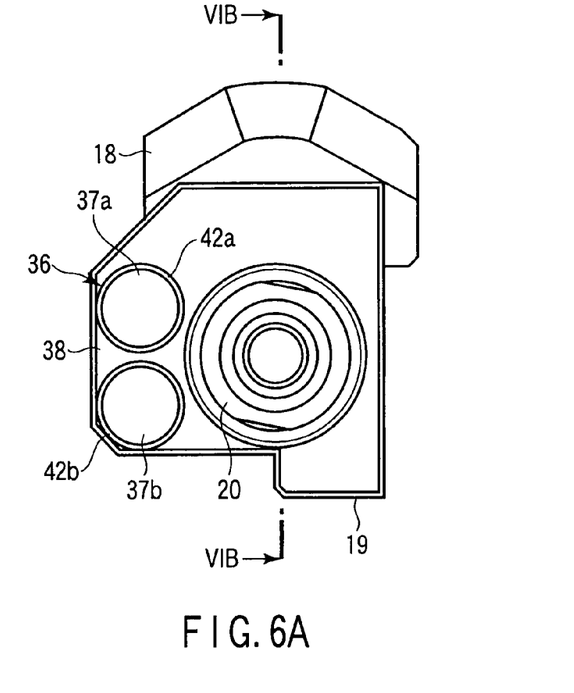
FIG. 6A is a front view showing a coupling member provided in a connection portion between a medical treatment instrument insertion channel and a medical treatment instrument insertion portion of an endoscope according to a second embodiment of the present invention.
Figure 6B:
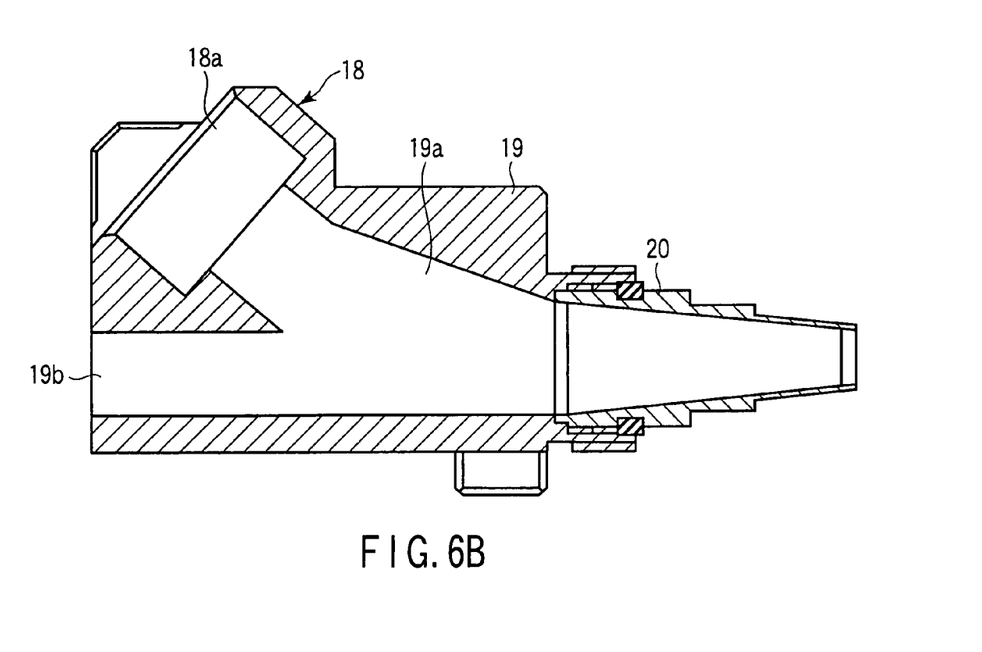
FIG. 6B is a sectional view along the line VIB-VIB in FIG. 6A.

FIG. 6A and FIG. 6B are diagrams showing a second embodiment of the present invention. According to the present embodiment, the configuration of a coupling member 19 provided in a connection portion between a medical treatment instrument insertion channel (not shown) of an endoscope 1 and a medical treatment instrument insertion portion 18 is modified as compared with the first embodiment (see FIG. 1 to FIG. 5B). According to the present embodiment, a branch path 19b that branches from a medical treatment instrument insertion path 19a is provided within the coupling member 19. The medical treatment instrument insertion path 19a and the branch path 19b are in communication with the medical treatment instrument insertion channel through a connection cap 20. The downstream side (opposite to the medical treatment instrument insertion path 19a) of the branch path 19b is in communication with a suction duct (not shown). The suction duct is coupled to a suction cap (not shown) provided in an operation portion 3.

Thus, when the other end of a suction tube (not shown) having one end connected to a suction device (not shown) is connected to the suction cap, the suction tube is in communication with the medical treatment instrument insertion channel via the suction duct and the branch path 19b. As a result, a suction operation can be performed via the medical treatment instrument insertion channel.

Third Embodiment

FIG. 7A to FIG. 8B are diagrams showing a third embodiment of the present invention. According to the present embodiment, the configuration of a movement regulating portion 36 which regulates the movement of a wire crossing portion 41 from within an operation portion 3 into an insertion portion 2 is modified as compared with the first embodiment (see FIG. 1 to FIG. 5B).

Figure 7A:
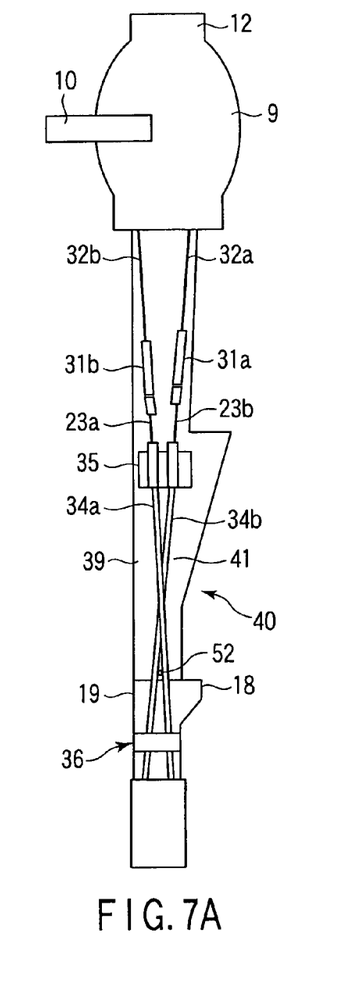
FIG. 7A is a schematic diagram showing the configuration of operation wires provided within an operation portion of an endoscope according to a third embodiment of the present invention in the second set condition.
Figure 7B:
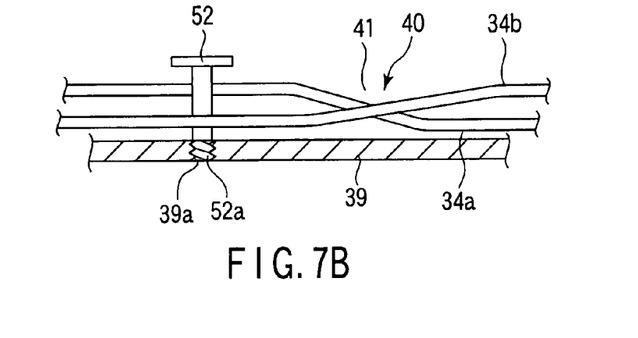
FIG. 7B is a longitudinal sectional view showing the attachment condition of a pin which regulates the movement of a wire crossing portion of the endoscope according to the third embodiment.

That is, according to the present embodiment, a pin 52 protrudes in a base plate 39 within the operation portion 3. The pin 52 is located to the position closer to the insertion portion 2 than the position of the wire crossing portion 41 of a first wire guide 34a and a second wire guide 34b. The pin 52 is provided between the first wire guide 34a and the second wire guide 34b in a direction perpendicular to a longitudinal direction. As shown in FIG. 7B, a male screw 52a is formed in the lower end of the pin 52. A screw hole 39a is formed in the base plate 39. The male screw 52a of the pin 52 is screwed into the screw hole 39a in the base plate 39 so that the pin 52 is fixed to the base plate 39. The pin 52 may be configured to be fixed to the base plate 39 by, for example, welding or bonding.

Figure 8A:
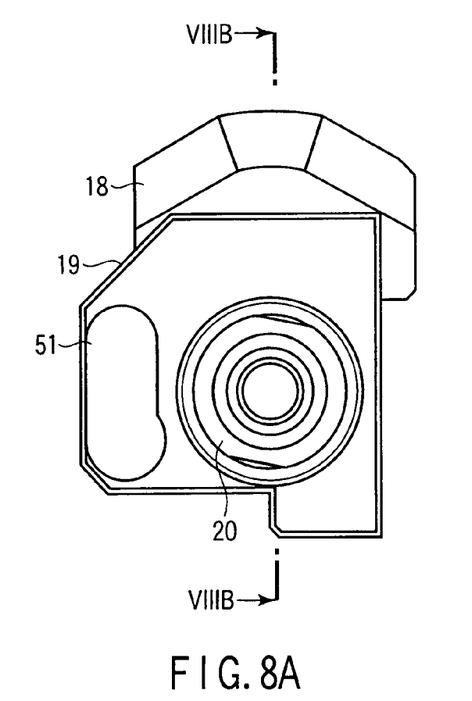
FIG. 8A is a front view showing a coupling member provided in a connection portion between a medical treatment instrument insertion channel and a medical treatment instrument insertion portion of the endoscope according to the third embodiment.
Figure 8B:
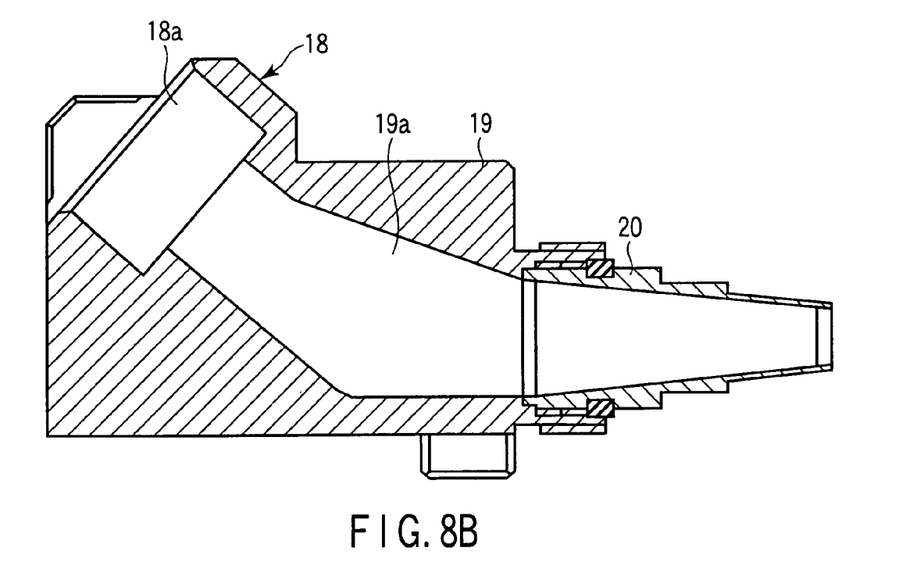
FIG. 8B is a sectional view along the line VIIIB-VIIIB in FIG. 8A.

As shown in FIG. 8A, according to the present embodiment, one long hole 51 is formed in a coupling member 19 provided in a connection portion between a medical treatment instrument insertion channel (not shown) of an endoscope 1 and a medical treatment instrument insertion portion 18. The first wire guide 34a and the second wire guide 34b are inserted through the long hole 51 together.

According to the present embodiment, the movement of the wire crossing portion 41 of the first wire guide 34a and the second wire guide 34b from within the operation portion 3 into the insertion portion 2 is regulated by the pin 52 fixed to the base plate 39. Thus, even when the curving operation is repeated, the movement of the wire crossing portion 41 from within the operation portion 3 into the insertion portion 2 can be prevented. This makes it possible to prevent the interference between the wire crossing portion 41 and components provided within the insertion portion 2 including an imaging cable, the medical treatment instrument insertion channel, a light guide, and an air/water supply tube. Thus, damage to the components provided within the insertion portion 2 including the imaging cable, the medical treatment instrument insertion channel, the light guide, and the air/water supply tube can be prevented.

Furthermore, according to the present embodiment, the movement of the wire crossing portion 41 from within the operation portion 3 into the insertion portion 2 can be prevented by the simple configuration in which the pin 52 protrudes from the base plate 39. Thus, costs of the overall curving mechanism 30 can be reduced.

The present invention is not limited to the embodiments described above. Although the curving portion 5 is a two-way curving type capable of curving in two directions in the embodiments described above, the present invention is, not limited thereto. For example, the present invention may be applied to an endoscope in which a curving portion 5 is a four-way curving type capable of curving in vertical and lateral directions when substantially horizontally extended. In this case, the set condition of a vertical curving mechanism which vertically curves the curving portion 5 and the set condition of a lateral curving mechanism which laterally curves the curving portion 5 can be changed as needed. Consequently, it is possible to provide an endoscope in which the relationship between the curving operation and the curving direction of the curving portion 5 is adaptable to user preference.

Now, other characteristic technical matters of the present application are additionally noted below:

(Additional note 1) An endoscopic operation portion including a curving operation portion, wherein a wire crossing portion is provided by crossing, within the operation portion, operation wires extending from an insertion portion and corresponding coils through which the operation wires are inserted, and the operation wires are connected to the curving operation portion in contrast with the case where the wire crossing portion is not provided.

(Additional note 2) The endoscopic operation portion according to Additional note 1, wherein a partition portion which partitions the coils is provided within the operation portion between the wire crossing portion and the proximal end of the insertion portion.

(Additional note 3) An endoscope comprising:
an insertion portion which includes a curving portion configured to curve in a first curving direction and in a second curving direction opposite to the first curving direction;
an operation portion provided in a proximal direction side to the insertion portion, the operation portion including a curving operation portion which is configured to perform a curving operation of the curving portion by rotating around a pivot shaft in a first rotation direction and in a second rotation direction opposite to the first rotation direction from a neutral position where the curving portion is in a non-curved neutral state;
a first operation wire which is pulled by the curving operation in the curving operation portion to curve the curving portion in the second curving direction;
a second operation wire which is pulled by the curving operation in the curving operation portion to curve the curving portion in the first curving direction;
a curving direction setting portion which is configured to set the relationship between the rotation direction of the curving operation portion and the curving direction of the curving portion to a first set condition or a second set condition, the first set condition being a condition in which the second operation wire is pulled by rotating the curving operation portion in the first rotation direction and in which the first operation wire is pulled by rotating the curving operation portion in the second rotation direction, the second set condition being a condition in which the first operation wire is pulled by rotating the curving operation portion in the first rotation direction and in which the second operation wire is pulled by rotating the curving operation portion in the second rotation direction, the curving direction setting portion including a wire crossing portion which is provided within the operation portion in the second set condition and in which the first operation wire and the second operation wire cross each other; and
a movement regulating portion which is provided within the operation portion and which is configured to regulate the movement of the wire crossing portion from within the operation portion into the insertion portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
an insertion portion which includes a curving portion configured to curve in a first curving direction and in a second curving direction opposite to the first curving direction;
an operation portion provided proximally of the insertion portion, the operation portion including an operation portion main body, and a curving operation portion which is configured to perform a curving operation of the curving portion by rotating around a pivot shaft in a first rotation direction and in a second rotation direction opposite to the first rotation direction relative to the operation portion main body from a neutral position where the curving portion is in a non-curved neutral state;
two draw-wires including:
a first draw-wire which is pulled by rotating the curving operation portion in the second rotation direction, and
a second draw-wire which is pulled by rotating the curving operation portion in the first rotation direction;
two operation wires including:
a first operation wire; and
a second operation wire,
the first operation wire and the second operation wire being configured to extend within the operation portion in one of a first extended condition or a second extended condition, selectively, the first extended condition being a condition in which the second operation wire is connected to the second draw-wire and in which the first operation wire is connected to the first draw-wire, the second extended condition being a condition in which the first operation wire is connected to the second draw-wire and in which the second operation wire is connected to the first draw-wire, the first operation wire being pulled in the first extended condition when the first draw-wire is pulled, and the first operation wire being pulled in the second extended condition when the second draw-wire is pulled, so as to curve the curving portion in the second curving direction, the second operation wire being pulled in the first extended condition when the second draw-wire is pulled, and the second operation wire being pulled in the second extended condition when the first draw-wire is pulled, so as to curve the curving portion in the first curving direction, and only in the second extended condition, the first operation wire and the second operation wire form a wire crossing portion within the operation portion in which the second operation wire crosses the first operation wire; and a movement regulating portion which is provided within the operation portion and which is fixed relative to the operation main body, the movement regulating portion being configured to prevent the wire crossing portion in the second extended condition from moving distally toward the insertion portion such that the wire crossing portion is prevented from moving into the insertion portion, wherein the operation portion includes a medical treatment instrument insertion portion in which a medical treatment instrument insertion path is formed, the medical treatment instrument insertion path being in communication with a medical treatment instrument insertion channel provided within the insertion portion, and the block includes a coupling member which is provided in the medical treatment instrument insertion portion and in which the medical treatment instrument insertion path is provided at a distance from the first inner peripheral surface portion and the second inner peripheral surface portion.

2. The endoscope according to claim 1, further comprising:

a wire drive portion which is provided within the operation portion, and which pivots together with the pivot shaft of the curving operation portion in accordance with the rotation of the curving operation portion to pull the first operation wire or the second operation wire;

a first wire guide through which the first operation wire is inserted;

a second wire guide through which the second operation wire is inserted, and which crosses the first wire guide in the wire crossing portion in the second extended condition; and a wire guide fixing portion provided so that the wire crossing portion is located between the wire guide fixing portion and the movement regulating portion in the second extended condition, a proximal end of the first wire guide and a proximal end of the second wire guide being fixed to the wire guide fixing portion.

* * * * *